United States Patent
Deimling

(10) Patent No.: US 8,463,009 B2
(45) Date of Patent: Jun. 11, 2013

(54) EVALUATION METHOD FOR A SERIES OF IMAGE DATA SETS WITH TWO-FOLD ELASTIC DISTORTION OF THE IMAGE DATA SETS

(75) Inventor: Michael Deimling, Moehrendorf (DE)

(73) Assignee: Siemens Aktiengesellschaft, Munich (DE)

( * ) Notice: Subject to any disclaimer, the term of this patent is extended or adjusted under 35 U.S.C. 154(b) by 260 days.

(21) Appl. No.: 13/080,096

(22) Filed: Apr. 5, 2011

(65) Prior Publication Data

US 2011/0249874 A1    Oct. 13, 2011

(30) Foreign Application Priority Data

Apr. 8, 2010   (DE) .......................... 10 2010 014 211

(51) Int. Cl.
*G06K 9/00* (2006.01)
*A61B 5/04* (2006.01)

(52) U.S. Cl.
USPC ............................ 382/128; 382/256; 600/509

(58) Field of Classification Search
USPC ................ 382/100, 103, 107, 128–134, 162, 382/168, 173, 181, 199, 232, 254, 256, 274, 382/276, 305, 312; 600/428, 509; 378/4, 378/21
See application file for complete search history.

(56) References Cited

U.S. PATENT DOCUMENTS

| | | | | | |
|---|---|---|---|---|---|
| 8,103,333 | B2 * | 1/2012 | Tran | | 600/509 |
| 8,275,448 | B2 * | 9/2012 | Camus et al. | | 600/428 |
| 8,315,447 | B2 * | 11/2012 | Hayes | | 382/128 |
| 2008/0226149 | A1 * | 9/2008 | Wischmann et al. | | 382/131 |
| 2009/0214090 | A1 | 8/2009 | Hayes | | |
| 2010/0061611 | A1 * | 3/2010 | Xu et al. | | 382/131 |

FOREIGN PATENT DOCUMENTS

| | | |
|---|---|---|
| DE | 10 2005 010 093 A1 | 9/2006 |
| DE | 10 2005 037 426 A1 | 2/2007 |

* cited by examiner

*Primary Examiner* — Seyed Azarian
(74) *Attorney, Agent, or Firm* — Schiff Hardin LLP

(57) ABSTRACT

A series of image data sets of a region of an organism is acquired while the acquired region of the organism moves dependent on breathing and heartbeat, and supplied to a processor. The processor determines a first contour that moves depending on the breathing in the acquired image data sets. The acquired image data sets are distorted elastically in the processor into singly distorted image data sets such that the first contours of the singly distorted image data sets spatially correspond with one another. A second contour is determined in the processor in the acquired image data sets or in the singly distorted image data sets, this second contour moves depending on the heartbeat. The singly distorted image data sets are distorted elastically into doubly distorted image data sets such that the second contours of the doubly distorted image data sets spatially correspond with one another. Regions of the doubly distorted image data sets that spatially correspond to one another are evaluated in the processor across image data sets.

8 Claims, 2 Drawing Sheets

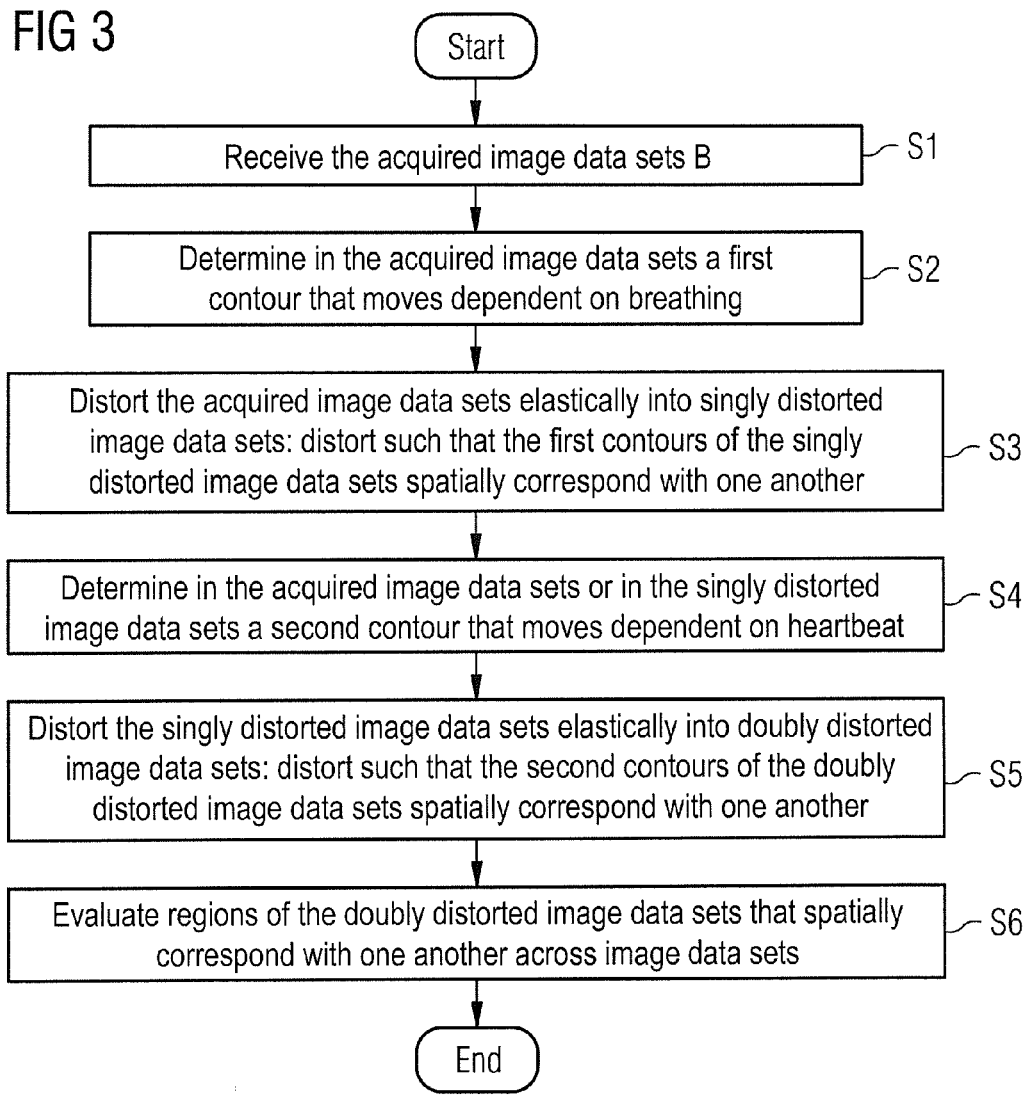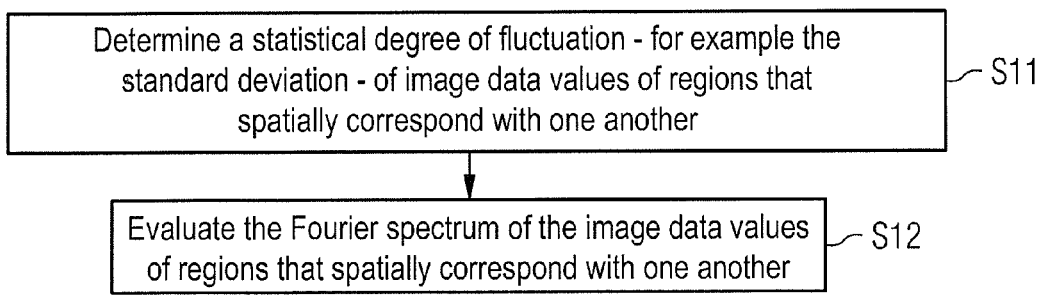

EVALUATION METHOD FOR A SERIES OF IMAGE DATA SETS WITH TWO-FOLD ELASTIC DISTORTION OF THE IMAGE DATA SETS

BACKGROUND OF THE INVENTION

1. Field of the Invention

The present invention concerns an evaluation method for a series of image data sets of a region of an organism, wherein the series of image data sets was acquired while the acquired region of the organism moved due to breathing and heartbeat.

The present invention furthermore concerns a computer program that embodies code that can be executed directly by a computer to execute such an evaluation method.

The present invention furthermore concerns a computer that is configured to execute such an evaluation method during operation.

2. Description of the Prior Art

An important diagnostic application of cardiac imaging is to reveal areas in the myocardium that have a reduced functional capacity. In particular, nuclear medical imaging with the modality is known as SPECT (Single Photon Emission Computed Tomography) has been established for this purpose. Furthermore, in the future it is expected that nuclear magnetic resonance tomography for such diagnostic applications will be increasingly used. Nuclear magnetic resonance tomography offers the advantages of a significantly better spatial resolution and the delivery of additional functional information, for example a prognosis of the recovery of the regional contraction capability of the heart, the mobility or the contraction-triggering state of the cardiac wall, etc.

An additional advantage of the nuclear magnetic resonance tomography is that ionizing radiation does not need to be used.

In the prior art, to show the functional capacity a contrast agent (for example a gadolinium agent) is administered and the tissue is examined after a certain time (in the minute range) with an appropriate measurement sequence. The contrast agent is in an enriching state at the points of the cardiac muscle at which the perfusion of the cardiac muscle is severely limited only after a delay following the time of administration (injection). The diseased area is therefore shown with higher signal than healthy tissue. This procedure is known in the prior art as "delayed enhancement".

A different acquisition method based on nuclear magnetic resonance methods is known as SPAMM (SPAtial Modulation of Magnetization). In this method an organized grid or stripe pattern is impressed on the cardiac region. In this case a reduced mobility of the myocardium appears in a deformation of the stripe or, respectively, grid structure within the time-resolved interval between two heartbeats.

The evaluations of the prior art are problematical because the region of the organism to be examined is moved. In particular, two superimposed movements are normally present, namely the lung movement induced by the movement of the diaphragm, and the heartbeat and the resulting movements caused thereby. Nearly all acquisition methods of the prior art are based on a movement-synchronized data acquisition, for example prospective or retrospective triggering and/or gating. A shortening of measurement time by an acquisition while the breath is being held is possible in some but not all cases.

SUMMARY OF THE INVENTION

An object of the present invention is to provide an evaluation method for a series of image data sets of a region of an organism in which neither a synchronization with the breathing-dependent movement nor a synchronization with the heartbeat-dependent movement is required.

According to the invention in an evaluation method of the aforementioned type

- a first contour is determined in the acquired image data sets, this first contour moving in correspondence with the breathing-dependent movement of the acquired region of the organism,
- the acquired image data sets are distorted elastically into singly distorted image data sets such that the first contours of the singly distorted image data sets spatially correspond with one another,
- a second contour is determined in the acquired image data sets or in the singly distorted image data sets, this second contour moving in correspondence with the heartbeat-dependent movement of the acquired region of the organism,
- the singly distorted image data sets are distorted elastically into doubly distorted image data sets such that the second contours of the doubly distorted image data sets spatially correspond with one another, and
- regions of the doubly distorted image data sets that spatially correspond to one another are evaluated across image data sets.

The first contour can be the lung contour of the organism or a rib contour of the organism. The second contour can be the heart contour of the organism.

The type of image data sets can be determined as needed. In particular, the image data sets alternatively can be two-dimensional image data sets or three-dimensional image data sets. Three-dimensional image data sets are preferred. The type of physical acquisition of the image data sets can also be determined as needed. X-ray techniques, ultrasound techniques and (preferably) magnetic resonance techniques can be considered as image data acquisition modalities.

The individual image data sets normally have a constant time offset. The time offset can be determined as needed, but it should be unequal to the cardiac period as well as unequal to the breathing period. The image data sets are advantageously acquired with a time offset that is smaller than the time interval between two heartbeats. For example, the image data sets can be acquired by means of a multislice 2D true FISP measurement sequence. Such a measurement sequence can deliver image data sets with a temporal resolution of 300 ms, and having a FoV (Field of View) of approximately 300 mm. If the measurement sequence is repeated over a longer period of time, the series of image data sets accumulates at a rate of approximately 3 image data sets per second. If a multi-channel array coil or a different parallel acquisition technique is additionally used, an acceleration by (for example) a factor of 4 is possible so that approximately 10 to 15 image data sets accumulate in one cardiac cycle. Such an image rate is high enough in order to be able to show the movement essentially continuously. In the event that it is necessary, the time resolution can be even further improved by time interpolation. Forty images or more are acquired per breathing cycle in this procedure.

The number of image data sets acquired in total can be according to need, for example over 100.

The type of evaluation can likewise be determined as needed. For example, the evaluation can include the determination of a statistical degree of fluctuation of image data values of the regions spatially corresponding with one another. One example of a suitable statistical degree of fluctuation is the standard deviation. Alternatively or additionally, the evaluation can include an evaluation of the Fourier spectrum of image data values of the regions spatially corresponding with one another. A stronger low-frequency portion of the Fourier spectrum in particular indicates a reduced mobility.

The evaluation methods according to the invention operate particularly reliably when the evaluated regions spatially corresponding with one another lie within the second contour.

The present invention furthermore encompasses a non-transitory computer-readable storage medium encoded with programming instructions that, when executed in a computer, cause an evaluation method according to the invention to be implemented. The data storage medium can be a component of the computer.

The object is furthermore achieved by a computer that is configured by programming and/or hardware to execute an evaluation method according to the invention during operation.

BRIEF DESCRIPTION OF THE DRAWINGS

FIG. 3 is a workflow diagram of an embodiment of the method according to the invention.

FIG. 5 is a workflow diagram of another embodiment of the method according to the invention.

DESCRIPTION OF THE PREFERRED EMBODIMENTS

Figure 1:
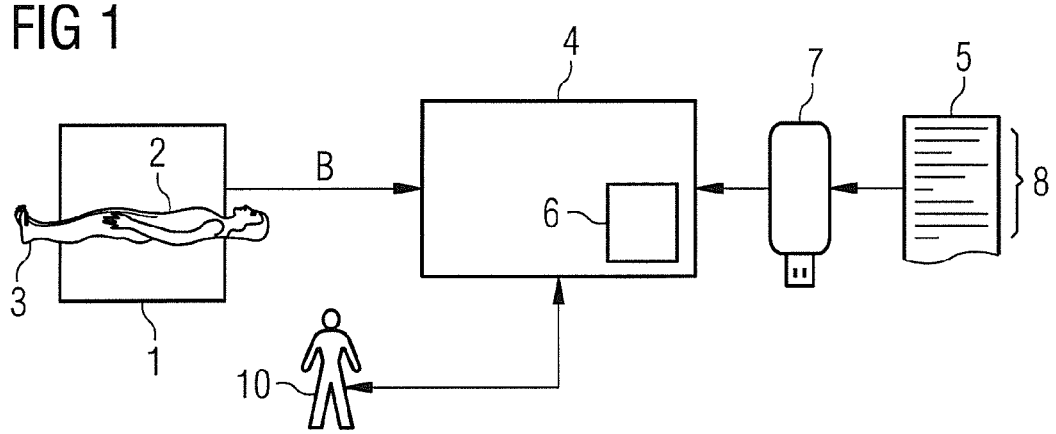
FIG. 1 is a block diagram of the basic components of san evaluation arrangement suitable for implementing the method according to the invention.

According to FIG. 1, a series of image data sets B of a region 2 of an organism 3 is acquired by means of a suitable image data acquisition device 1. The acquired region 2 is selected such that the acquired region 2 of the organism 3 moves both dependent on breathing and dependent on heartbeat. For example, the acquired region 2 of the organism 3 can correspond to the heart-lung region of the organism 3. The two cited movements of the region 2 of the organism 3 also take place during the acquisition of the image data sets B.

The type of acquisition device 1 and the type of image data sets B can be selected as needed. For example, the image data sets B can be three-dimensional image data sets that are acquired by means of a magnetic resonance system. Alternatively, the image data sets B can be two-dimensional in nature. The acquisition device 1 can also realize a different type of acquisition that, for example, is based on x-ray techniques or on ultrasound techniques. The acquired image data sets B can be two-dimensional or (preferably) three-dimensional.

Figure 2:
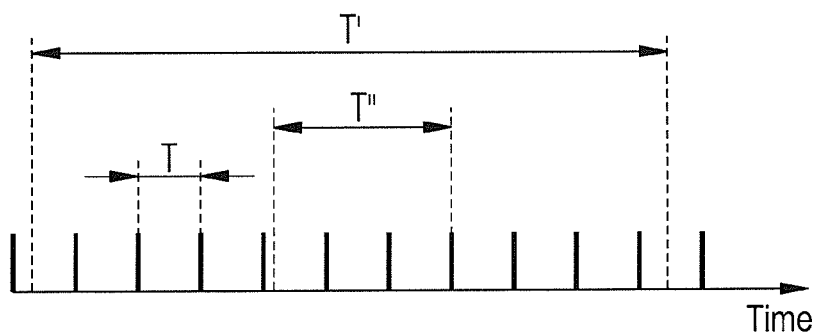
FIG. 2 is a time diagram for explaining the basis of the method according to the invention.

According to FIG. 2, the image data sets B are normally acquired with a fixed time offset T. In individual cases it is possible that the time offset T is greater than the duration T' of a breathing period. However, the time offset T is normally smaller than the duration T' of the breathing period, often even significantly smaller. The time offset T is normally even smaller than the duration T'' of a cardiac period. For example, 10 to 15 image data sets can be acquired per heartbeat 10. The techniques required for this are known to men skilled in the art. For example, in magnetic resonance systems the aforementioned multislice 2D true FISP can be used in connection with a parallel acquisition technique (multichannel array coil or the like).

The number of image data sets B can be determined as needed. In many cases the number will be greater than 100.

The acquired image data sets B are supplied to a computer 4. The computer 4 is configured to evaluate the image data sets B as described in the following. To evaluate the image data sets B, the computer 4 executes a computer program 5 with which the computer 4 is programmed and the mode of operation of the computer 4 is determined.

The computer program 5 is stored within the computer 4 in a data medium 6, for example on the hard drive of the computer 4. The data medium 6 is a component of the computer 4. The storage takes place in a machine-readable form, most often even in an exclusively machine-readable form.

The computer program 5 can be supplied to the computer 4 by means of a portable data medium 7, for example a USB memory stick (shown) or an SD memory card (not shown) or another suitable portable data medium 7. The computer program 5 is stored on the portable data medium 7 in machine-readable form. Alternatively, it is possible to supply the computer program 5 to the computer 4 via a computer network connection.

The computer program 5 embodies machine code 8 that can be executed directly by the computer 4. The execution of the machine code 8 by the computer 4 has the effect that the computer 4 executes an evaluation method according to the invention. This evaluation method is subsequently explained in detail in connection with FIG. 3.

According to FIG. 3, the computer 4 initially receives the acquired image data sets B in Step S1.

A first contour 9 (see FIG. 4) in the acquired image data sets B is determined in Step S2. The first contour 9 is characterized by moving in a manner corresponding to the breathing-dependent movement of the acquired region 2 of the organism 3.

The first contour 9 can be determined as needed. In many cases it is the contour of the lung and/or of the ribs of the organism 3, corresponding to the depiction of FIG. 4. Alternatively, Step 2 can be executed wholly automatically by the computer 4 or interactively with interaction of a user 10 (see FIG. 1).

In Step S3 the acquired image data sets B are elastically distorted. The elastically distorted image data sets are subsequently designated as singly distorted image data sets and provided with the reference character B' in order to be able to differentiate them from the acquired, undistorted image data sets B. The distortion of the acquired image data sets B takes place in Step S3 such that the first contours 9 of the singly distorted image data sets B' spatially correspond with one another. Elastic distortion methods as such are known to men skilled in the art. Therefore distortion methods do not need to be discussed in detail herein.

To implement Step 3, one of the acquired image data sets B is normally determined as a reference image data set. This one acquired image data set B (i.e. the reference image data set) remains undistorted. The other image data sets B are distorted corresponding to the aforementioned rule.

The reference image data set can in principle be determined arbitrarily. However, the reference image data set is normally determined such that it is an average image data set in relation to the movement of the first contour 9. For example, in particular one of those image data sets B in which the breathing-dependent movement is located approximately in the middle between inhaled and exhaled state can be used as a reference image data set. The selection of the correspondingly acquired image data set B alternatively can take place automatically or interactively with interaction by the user 10. The distortion of the remaining image data sets B is normally executed wholly automatically by the computer 4.

After execution of Step S3, the first contours 9 of the singly distorted image data sets B' spatially correspond with one another.

A second contour 11 (see FIG. 4) is now determined in Step S4. The determination of Step S4 can alternatively be conducted in the acquired image data sets B or in the singly distorted image data sets B'. Analogous to Step S2, Step S4 alternatively can be executed automatically or interactively with interaction by the user 10. In the event that the second contour 11 is determined in the acquired image data sets B, Step S4 can be executed before Step S3 and even before Step S2.

The second contour 11 is determined as a contour that moves corresponding to the heartbeat-dependent movement of the acquired region 2 of the organism 3. The second contour 1 can be the heart contour itself or alternatively a different contour can be used.

In Step S5 the singly distorted image data sets B' is distorted again and thus doubly distorted image data sets B" are generated. The doubly distorted image data sets are subsequently provided to differentiate between the acquired image data sets B and the singly distorted image data sets B' with the reference character B".

The distortion of Step S5 takes place such that the second contours 11 of the image data sets B spatially correspond with one another. Its implementation can be analogous to that of Step S3.

Within Step S5, one of the singly distorted image data sets B' is often determined as a reference data set (analogous to Step S3) relative to which the other singly distorted image data sets B' are distorted. Analogous to the procedure within the scope of Step S3, a singly distorted image data set B' is determined relative to the reference data set in which a middle movement state of the second contour 11 is present, thus between a maximum contraction of the heart and a maximum relaxation of the heart. The reference image data set for the execution of Step S5 can be identical to the reference image data set for the execution of Step S3. However, it is not absolutely necessary. Alternatively it can be a different image data set that was already distorted within the scope of Step S3.

Step S5 is normally executed wholly automatically by the computer 4. The determination of the reference image data set can possibly take place only with interaction by the user 10.

Regions 12 of the doubly distorted image data sets B" (see FIG. 4) that spatially correspond with one another are evaluated across image data sets in Step S6.

The type of evaluation of Step S6 can be determined as needed. For example, to implement Step S6 the determination of a statistical degree of fluctuation—for example the standard deviation—of image data values of the regions 12 spatially corresponding to one another can be conducted corresponding to FIG. 5. The regions 12 can be determined as needed. These can be individual pixels or voxels or groups of adjacent pixels or voxels. If the statistical degree of fluctuation is above a specific threshold, the corresponding region 12 can be classified as "healthy", for example. If the statistical degree of fluctuation is below the limit, the corresponding region 12 can be variably classified as pathological.

Insofar as it pertains to the determination of the statistical degree of fluctuation and the comparison with the determined threshold, Step S11 can be executed automatically by the computer 4. Naturally, the diagnostic classification itself must be made by the user 10. The threshold can be hard-set or be adjustable by the user 10.

Alternatively or additionally, to implement Step S6 an evaluation of the Fourier spectrum of the image data values of the corresponding regions 12 can be conducted according in Step 12 according to FIG. 5. In this case, the weight to be accorded to a null frequency—thus corresponds to a constant component—can be determined in particular. The greater this weight, the greater the probability that a pathological variation is present.

Step S12 can be executed automatically by the computer 4, analogous to Step S11 with regard to the determination of the Fourier spectrum and the weighting of individual frequency ranges, but the diagnostic classification itself must be made by the user 10.

Figure 4:
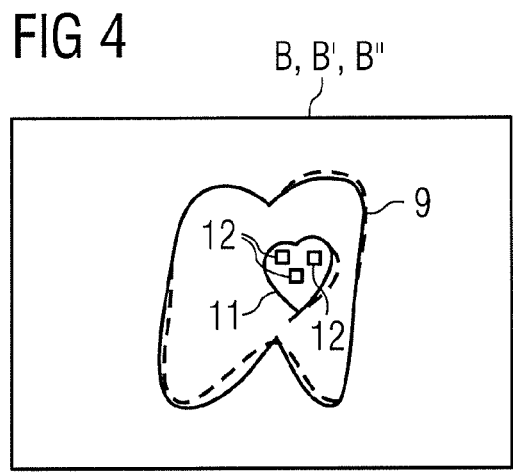
FIG. 4 schematically illustrates an example of an image data set created according to the inventive method.

The regions 12 that are evaluated in the doubly distorted image data sets B" can in principle be arranged arbitrarily, but they normally lie within the second contour 11 corresponding to the depiction from FIG. 4.

The present invention has many advantages. In particular, within the scope of the evaluation method according to the invention it is not required to conduct a breath gating. It is also not required to synchronize the image data sets B with the heartbeat. Depending on the type of data acquisition it can even be possible to work without contrast agent. Furthermore, it is not necessary to use ionizing radiation.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computerized evaluation method for a series of image data sets of a region of an organism, comprising the steps:
   supplying a series of image data sets to a computerized processor that were acquired while a region of the organism represented by the image data sets moved dependent on breathing and heartbeat;
   in said processor, determining a first contour in the acquired image data sets that moved corresponding to the breathing-dependent movement of the acquired region of the organism;
   in said processor, elastically distorting the acquired image data sets into singly distorted image data sets to cause the first contours of the singly distorted image data sets to spatially correspond with one another;
   in said processor, determining a second contour in the acquired image data sets or in the singly distorted image data sets that moved corresponding to the heartbeat-dependent movement of the acquired region of the organism;
   in said processor, elastically distorting the singly distorted image data sets into doubly distorted image data sets to cause the second contours of the doubly distorted image data sets to spatially correspond with one another; and
   in said processor, evaluating regions of the doubly distorted image data sets that spatially correspond to one another across respective image data sets to generate an evaluation result, and making said evaluation result available in electronic form at an output of said processor.

2. An evaluation method as claimed in claim 1, comprising supplying the image data sets to said processor as three-dimensional image data sets.

3. An evaluation method as claimed in claim 1 comprising evaluating said doubly distorted image data sets by determining a statistical degree of fluctuation of image data values of the regions spatially corresponding with one another.

4. An evaluation method as claimed in claim 3 comprising determining the standard deviation of said image data values of the regions spatially corresponding with each other, as said statistical degree of fluctuation.

5. An evaluation method as claimed in claim 1 evaluating a Fourier spectrum of image data values of the regions spatially corresponding with one another.

6. An evaluation method as claimed in claim 1 comprising evaluating said doubly distorted image data sets by evaluating regions, as regions that spatially correspond with one another that a lie within the second contour.

7. A non-transitory computer-readable storage medium encoded with programming instructions for evaluating a series of image data sets of a region of an organism, said series of image data sets having been acquired while the region of the organism moved dependent on breathing and heartbeat, said storage medium being loaded into a computer and said series of image data sets being supplied to the computer, and said programming instructions causing the computer to:
   determine a first contour in the acquired image data sets that moved corresponding to the breathing-dependent movement of the acquired region of the organism;
   elastically distort the acquired image data sets into singly distorted image data sets to cause the first contours of the singly distorted image data sets to spatially correspond with one another;
   determine a second contour in the acquired image data sets or in the singly distorted image data sets that moved corresponding to the heartbeat-dependent movement of the acquired region of the organism;
   elastically distort the singly distorted image data sets into doubly distorted image data sets to cause the second contours of the doubly distorted image data sets to spatially correspond with one another; and
   evaluate regions of the doubly distorted image data sets that spatially correspond to one another across respective image data sets to generate an evaluation result, and make said evaluation result available in electronic form at an output of said processor.

8. A computer for evaluating a series of image data sets of a region of an organism, said computer comprising:
   an input supplied with a series of image data sets to a computerized processor that were acquired while a region of the organism represented by the image data sets moved dependent on breathing and heartbeat;
   a processor configured to determine a first contour in the acquired image data sets that moved corresponding to the breathing-dependent movement of the acquired region of the organism;
   said processor being configured to elastically distort the acquired image data sets into singly distorted image data sets to cause the first contours of the singly distorted image data sets to spatially correspond with one another;
   said processor being configured to determine a second contour in the acquired image data sets or in the singly distorted image data sets that moved corresponding to the heartbeat-dependent movement of the acquired region of the organism;
   said processor being configured to elastically distort the singly distorted image data sets into doubly distorted image data sets to cause the second contours of the doubly distorted image data sets to spatially correspond with one another; and
   said processor being configured to evaluate regions of the doubly distorted image data sets that spatially correspond to one another across respective image data sets to generate an evaluation result, and to make said evaluation result available in electronic form at an output of said processor.

* * * * *